US012624065B2

(12) United States Patent　　(10) Patent No.:　US 12,624,065 B2
Ippoliti et al.　　　　　　　　　　(45) Date of Patent:　　May 12, 2026

(54) USE OF NEUTRAL pH MOBILE PHASES IN REVERSED PHASE CHROMATOGRAPHY OF ACIDIC PEPTIDES

(71) Applicant: Waters Technologies Corporation, Milford, MA (US)

(72) Inventors: Samantha Ippoliti, Franklin, MA (US); Ying Qing Yu, Uxbridge, MA (US)

(73) Assignee: Waters Technologies Corporation, Milford, MA (US)

( * ) Notice: Subject to any disclaimer, the term of this patent is extended or adjusted under 35 U.S.C. 154(b) by 434 days.

(21) Appl. No.: 17/858,496

(22) Filed: Jul. 6, 2022

(65) Prior Publication Data

US 2023/0009990 A1　　Jan. 12, 2023

Related U.S. Application Data

(60) Provisional application No. 63/218,694, filed on Jul. 6, 2021.

(51) Int. Cl.
| | |
|---|---|
| *C07K 1/20* | (2006.01) |
| *B01D 15/32* | (2006.01) |
| *C07K 1/22* | (2006.01) |
| *G01N 30/28* | (2006.01) |
| *G01N 30/36* | (2006.01) |
| *G01N 30/72* | (2006.01) |
| *G01N 30/88* | (2006.01) |
| G01N 30/02 | (2006.01) |
| G01N 30/84 | (2006.01) |

(52) U.S. Cl.
CPC .............. *C07K 1/20* (2013.01); *B01D 15/325* (2013.01); *C07K 1/22* (2013.01); *G01N 30/28* (2013.01); *G01N 30/7233* (2013.01); *G01N 2030/027* (2013.01); *G01N 30/36* (2013.01); *G01N 2030/8441* (2013.01); *G01N 2030/8831* (2013.01)

(58) Field of Classification Search
CPC .......... C07K 1/20; C07K 1/22; B01D 15/325; B01D 15/166; B01D 15/245; G01N 30/28; G01N 30/7233; G01N 2030/027; G01N 2030/8441; G01N 2030/34; G01N 30/36; G01N 30/72; G01N 2030/8831
See application file for complete search history.

(56) References Cited

U.S. PATENT DOCUMENTS

| | | | | |
|---|---|---|---|---|
| 2005/0170525 A1* | 8/2005 | Kuroda | .................... | B01J 20/06 |
| | | | | 436/514 |
| 2012/0264688 A1* | 10/2012 | Hinderer | .................. | A61P 7/06 |
| | | | | 530/397 |
| 2019/0086371 A1* | 3/2019 | Lauber | ................... | B01J 20/291 |
| 2020/0386722 A1 | 12/2020 | Birdsall et al. | | |
| 2021/0164094 A1 | 6/2021 | Shiner et al. | | |

FOREIGN PATENT DOCUMENTS

| | | | | |
|---|---|---|---|---|
| EP | 1477800 A1 | 11/2004 | | |
| EP | 3015473 A1 * | 5/2016 | ............. | B01D 15/12 |

OTHER PUBLICATIONS

Winkler and Marme, "Titania as a sorbent in normal-phase liquid chromatography." Journal of chromatography. vol. 888, 1-2, 2000: 51-62. doi: 10.1016/s0021-9673(00)00489-1. (Particularly Table 1, p. 54) (Year: 2000).*

Birdsall, et al., 2021. "Reducing metal-ion mediated adsorption of acidic peptides in RPLC-based assays using hybrid silica chromatographic surfaces". Journal of Chromatography B, 1179, p. 122700. DOI: https://doi.org/10.1016/j.jchromb.2021.122700 (8 pages total) (Year: 2021).*

Song et al. "Reversed-phase-reversed-phase liquid chromatography approach with high orthogonality for multidimensional separation of phosphopeptides". Analytical chemistry, 82(1), 2010—Supplemental Material (included on IDS filed Feb. 20, 2025; 1 page total) (Year: 2010).*

Dolan, J.M. "A Guide to HPLC and LC-MS Buffer Selection", ACE® HPLC Columns, available online as early as 2014, accessed from Wayback Machine, on Nov. 13, 2024 https://web.archive.org/web/20140418182135/https://www.hplc.eu/Downloads/ACE_Guide_BufferSelection.pdf (20 pages total) (Year: 2014).*

Medzihradszky et al. "Characterizing sialic acid variants at the glycopeptide level." Analytical chemistry, 87(5), 2015. 3064-3071. (Year: 2015).*

"Thermo Scientific Hypersil GOLD HPLC Columns Phase Overview", copyright 2016, Thermo Scientific Product Brochure, PDF obtained from https://assets.thermofisher.com/TFS-Assets/CMD/brochures/BR-21493-LC-Hypersil-GOLD-Phase-Overview-BR21493-EN.pdf, accessed on Nov. 12, 2024. (8 pages total) (Year: 2016).*

Wen et al. "Sialylated glycoproteins as biomarkers and drivers of progression in prostate cancer." Carbohydrate Research 519 (2022): 108598 (11 pages total) (Year: 2022).*

Song et al. "Reversed-phase-reversed-phase liquid chromatography approach with high orthogonality for multidimensional separation of phosphopeptides". Analytical chemistry, 82(1), 2010, pp. 53-56 (first available online Dec. 1, 2009) (Year: 2009).*

Kowalewska et al. "Electron capture dissociation mass spectrometric analysis of lysine-phosphorylated peptides". Biosci Rep Dec. 1, 2010; 30 (6): 433-443. doi: 10.1042/BSR20090167 (Year: 2010).*

"Vydac 218TP C18, HPLC columns", Avantor®, accessed from <www.avantorsciences.com/ie/en/product/22111866/hplc-columns-vydac-218tp-c18/> on Aug. 7, 2025. Publication date unknown, 6 pages total. (Year: 2025).*

Ohta et al. "Selective glycopeptide mapping of erythropoietin by on-line high-performance liquid chromatography—electrospray ionization mass spectrometry." Journal of chromatography. A vol. 910,1 (2001): 1-11. doi:10.1016/s0021-9673(00)01116-x. (Year: 2001).*

(Continued)

*Primary Examiner* — Anand U Desai
*Assistant Examiner* — Andrew T Moehlman
(74) *Attorney, Agent, or Firm* — WOMBLE BOND DICKINSON (US) LLP; Deborah M. Vernon

(57) ABSTRACT

The present disclosure discusses a method of separating and/or purifying acidic peptides by the use of a mobile phase having a pH greater than or about equal to the isoelectric point of one or more of the metal oxides in the flow path.

12 Claims, 7 Drawing Sheets

(56) References Cited

OTHER PUBLICATIONS

Houel et al. "N- and O-Glycosylation Analysis of Etanercept Using Liquid Chromatography an Quadrupole Time-of-Flight Mass Spectrometry Equipped with Electron-Transfer Dissociation Functionality" Anal Chem. 2014, 86, 576-584, on IDS filed Oct. 25, 2022 (Year: 2014).*

Lin et al. "Supercharging reagent for enhanced liquid chromatographic separation and charging of sialylated and high-molecular-weight glycopeptides for nanoHPLC-ESI-MS/MS analysis." Analytical chemistry 88.17 (2016): 8484-8494 (Year: 2016).*

Maa et al. "Rapid Analysis of Proteins and Peptides by Reversed-Phase Chromatography with Poylmeric Micropellicular Sorbents" J. Chromatogr. 445(1988): 71-86.

Matsumoto et al. "Separation of Phosphopeptides from Their Nonphosphorylated Forms by Reversed-Phase POROS Perfusion Chromatography at Alkaline pH." Anal. Biochem. 251.1(1997): 116-119.

Song et al. "Reversed-Phase-Reversed-Phase Liquid Chromatography Approach with High Orthogonality for Multidimensional Separation of Phosphopeptides." Anal. Chem. 82(2010): 53-56.

Houel et al. "N- and O-Glycosylation Analysis of Etanercept Using Liquid Chromatography an Quadrupole Time-of-Flight Mass Spectrometry Equipped with Electron-Transfer Dissociation Functionality." Anal Chem. 86(2014): 576-584.

Yang et al. "Analysis of peptides and protein digests by reversed phase high performane liquid chromatography-electrospray ionisation mass spectrometry using neutral pH elution conditions." Anal. Chim. Acta. 872(2015): 84-94.

Yang et al. "Peptide mapping with mobile phases of intermediate pH value using capillary reversed-phase high-performance liquid chromatography/electrospray ionisation tandem mass spectrometry." J. Chromatogr. A. 1216(2009): 3767-3773.

Song et al. "Reversed-Phase-Reversed-Phase Liquid Chromatography Approach with High Orthogonality for Multidimensional Separation of Phosphopeptides." Anal. Chem. 82(2010): 53-56—Supplemental Material.

Trinidad et al. "Global Identification and Characterization of Both O-GlcNAcylation and Phosphorylation at the Murine Synapse." Mol. Cell Prot. 11.8(2012): 215-229.

* cited by examiner

USE OF NEUTRAL pH MOBILE PHASES IN REVERSED PHASE CHROMATOGRAPHY OF ACIDIC PEPTIDES

This application claims the benefit of and priority to U.S. Provisional Patent Application Ser. No. 63/218,694 filed on Jul. 6, 2021 and entitled "Use of Neutral pH Mobile Phases in Reversed Phase Chromatography of Acidic Peptides," the contents of which are incorporated herein in their entirety.

FIELD OF THE TECHNOLOGY

The present disclosure relates to the use of a neutral pH mobile phase for improved chromatography and sample analysis of acidic peptides.

BACKGROUND

Analytes that interact with metals have often proven to be very challenging to separate. The desire to have high pressure capable chromatographic systems with minimal dispersion has required that flow paths decrease in diameter and be able to withstand increasingly high pressures at increasingly fast flow rates. As a result, the material of choice for chromatographic flow paths is often metallic in nature. This is despite the fact that characteristics of certain analytes, for example, small molecule pharmaceutical agents, proteins, peptides, glycopeptides, phosphopeptides, oligonucleotides, pesticides, bisphosphonic acids, anionic metabolites, and zwitterions like amino acids and neurotransmitters, are known to have unfavorable interactions, so called chromatographic secondary interactions, with metallic surfaces.

Significant loss of acidic peptide analytes, such as phosphopeptides and sialylated glycopeptides, is observed when using conventional reversed phase liquid chromatography (RPLC)—mass spectrometry (MS) methods. This is believed to be due to chelation interactions between the acidic peptides and the column/system hardware. Traditional RPLC-MS peptide mapping chromatographic methods typically use C18 column chemistry with mobile phases generally comprising water, acetonitrile, and formic acid. The formic acid is added to the mobile phase to boost the electrospray ionization (ESI+) of analytes, increasing the sensitivity of mass spectrometry detection. Unfortunately, under acidic pH mobile phase conditions, the acidic peptides interact with metal oxides in the liquid chromatography (LC) flow path via chelation reactions. The binding strength to metals in the LC flow path increases as the number of acidic residues on the peptide increases. In the case of sialylated O-glycopeptides, when the sialylation is greater than 2 per peptide, traditional RPLC-MS chromatographic methods cannot recover the analytes from the column. Glycopeptides and phosphopeptides, therefore, suffer significant or complete loss of signal in a typical RPLC-MS analysis. For the sialylated glycopeptides, the peptide mass spectrometry signals can be recovered after removing the sialic acids by enzymatic treatment. However, such sample treatment leads to missed information on the sialic acid location and quantity.

An alternative to using metal flow paths is to use flow paths constructed from polymeric materials, such as polyether ether ketone (PEEK). PEEK tubing, like most polymeric materials, is formed by means of an extrusion process. This manufacturing process can lead to highly variable internal diameters. Accordingly, PEEK column hardware yields unfavorable differences in the retention times as can be observed from switching between one column and the next. Often, this variation can be a factor of three higher than a metal constructed column.

Ongoing efforts to reduce chelation and secondary chromatographic interactions of acidic peptides with metal oxides in chromatographic flow paths, in an effort to facilitate chromatographic separation having higher resolutions, are therefore needed.

SUMMARY

Problems associated with the analysis of acidic peptides can be resolved by the use of a mobile phase having a pH greater than or about equal to the isoelectric point of one or more metal oxides in the flow path. The use of such a mobile phase is believed to reduce the amount of positively charged metal oxides in the flow path, which inhibits potential ion exchange reactions between the acidic peptides and the metal oxides. This, in turn, leads to a reduction in loss of acidic peptide samples.

In one embodiment, a method of separating and/or purifying acidic peptides comprises injecting a sample comprising one or more acidic peptides into a chromatographic system. The chromatographic system comprises a flow path. At least a portion of the flow path comprises one or more metal oxides. The sample is flowed through the chromatographic system under reverse phase chromatography conditions using a mobile phase having a pH greater than or about equal to the isoelectric point of one or more of the metal oxides in the flow path. Use of a mobile phase having a pH greater than or about equal to the isoelectric point of one or more of the metal oxides in the flow path allows acidic peptides to be analyzed using RPLC. Exemplary acidic peptides that can be analyzed using this technique include, but are not limited to, sialylated glycopeptides and phosphopeptides.

In an embodiment, the mobile phase used for RPLC comprises an acetate salt dissolved in water. The mobile phase, in some embodiments, is a buffered aqueous solution. The mobile phase has a pH of greater than or equal to 6. For example, the mobile phase can have a pH between 7 and 8.

The method also includes passing a fluid stream exiting the chromatographic column to a detector, the fluid stream comprising one or more of the acidic peptides. In some embodiments, an acidic solution is added to the fluid stream prior to passing the fluid stream to the detector. The acidic solution can comprise formic acid. The concentration of acid in the acidic solution can range from about 1% to 20% by volume in water. The acid solution may be added to the fluid stream by combing the flow of the fluid stream with a stream from the acid solution. The ratio of the flow rate of the acidic solution to the flow rate of the fluid stream is between about 1:100 and about 1:5. Addition of an acidic solution to the fluid stream is particularly useful when the detector is a mass spectrometer.

In some embodiments, at least a portion of the flow path is coated with a low-bind surface coating. The low-bind surface coating comprises an alkylsilyl coating.

In an embodiment, a chromatography system comprises: a pump; a chromatographic column; a diverter valve coupled to an outlet of the chromatographic column; an acidic fluid source coupled to the diverter valve; and a detector coupled to the diverter valve. During use, the acidic fluid source is mixed with a sample fluid exiting from the outlet of the chromatographic column such that a mixed fluid comprising a mixture of the acidic fluid source and the sample fluid exits the diverter valve and passes to the detector. The chromatographic system may be a high performance liquid chromatography system. The detector may be a mass spectrometer.

BRIEF DESCRIPTION OF THE DRAWINGS

The technology will be more fully understood from the following detailed description taken in conjunction with the accompanying drawings, in which.

DETAILED DESCRIPTION

Figure 1:
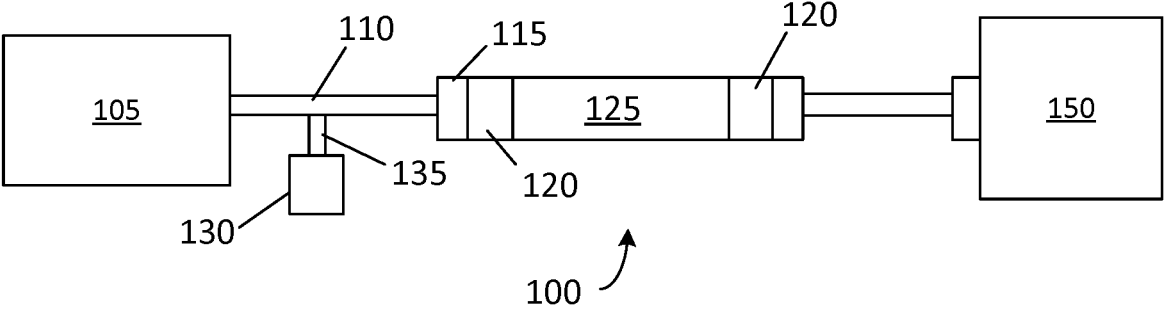
FIG. 1 is a schematic of a chromatographic flow system including a chromatography column and various other components, in accordance with an illustrative embodiment of the technology. A fluid is carried through the chromatographic flow system with a fluidic flow path extending from a fluid manager to a detector, such as a MS detector.

Adsorption of acidic peptides to metal surfaces has long been a problem in chromatography. Previous mitigation strategies have included passivation of surfaces, use of mobile phase additives, as well as the incorporation of inert hardware materials. While successful to some degree, these strategies have their drawbacks. Passivation of surfaces with either a strong acid, or with sample and/or matrix conditioning are time consuming, require the use of strong acids, and are not long-lived. Mobile phase additives such as chelators can help to prevent analyte-metal adsorption but also have drawbacks including ion suppression, possible solubility issues, and the fact that they must be continually used to remain effective. PEEK columns or PEEK lined steel columns replace the metal surfaces with non-reactive material, but PEEK alone is not tolerant of high-pressure use, and PEEK materials have higher dimensional variability, lower frit permeability, and are incompatible with some solvents.

More recently, columns featuring titanium hardware are now being offered commercially as a more bioinert alternative to conventional stainless-steel columns. Titanium is resistant to corrosion and is inert to some compounds. However, due to its metallic nature, it too can cause analyte adsorption and thus sample loss. Additionally, when used with methanol mobile phases, titanium has been found to leach metal ions.

These problems associated with the analysis of acidic peptides can be resolved by the use of a mobile phase having a pH greater than or about equal to the isoelectric point of one or more of the metal oxides in the flow path. The use of such a mobile phase is believed to reduce the amount of positively charged metal oxides in the flow path, which inhibits potential ion exchange reactions between the acidic peptides and the metal oxides. This, in turn, leads to a reduction in loss of acidic peptide samples.

Acidic peptides, as used herein, generally refers to peptides having a larger number of acidic amino acids (e.g., aspartic acid and glutamic acid) than basic amino acids (e.g., lysine, arginine and histidine). Peptides can also be made acidic by covalent modification of the peptide with acidic sugars (e.g., sialylated glycopeptides) and phosphates (e.g., phosphopeptides).

"Phosphopeptide" or "Phosphorylated peptide" refers to a peptide that has been covalently modified by one or more phosphate groups. Typically, tyrosine, serine and threonine hydroxyl groups are phosphorylated in a phosphopeptide. Covalent modification of a peptide by adding phosphate groups can render the peptide acidic.

"Glycopeptides" are peptides which contain a sugar (e.g., a monosaccharide or polysaccharide) covalently attached to amino acids of the peptides. There are several sites of glycosylation of peptides. N-glycosylated peptides have a sugar attached to a nitrogen of an amino acid side chain. O-glycosylated peptides have a sugar attached to an oxygen of an amino acid side chain. Less common glycosylation of peptides include P-glycosylation, C-glycosylation, and S-glycosylation of amino acids in the peptide. Monosaccharides commonly found in glycopeptides include, but are not limited to, glucose, galactose, mannose, fucose, acetylgalactosamine, acetlyglucosamine, sialic acids (e.g., N-acetyl-neuraminic acid), and xylose.

"Sialic acids" are nine-carbon carboxylated sugars. Members of the sialic acid family include, but are not limited to, N-acetyl-neuraminic acid (2-keto-5-acetamido-3,5-dideoxy-D-glyc-ero-D-galactononulopyranos-1-onic acid (abbreviated as NeuSAc, NeuAc, or NANA)), N-glycolyl-neuraminic acid (Neu5Gc or NeuGc), 2-keto-3-deoxy-nonulosonic acid (KDN). Sialic acids also include 9-substituted sialic acids such as a 9-O—$C_1$-$C_6$ acyl-Neu5Ac, 9-O-lactyl-Neu5Ac, 9-O-acetyl-NeuSAc, 9-deoxy-9-fluoro-Neu5Ac, and 9-azido-9-deoxy-Neu5Ac.

A "sialylated peptide" is a peptide that is modified by the covalent addition of one or more sialic acid moieties. "Sialylated glycopeptides" are glycopeptides that have been further modified by the covalent addition of one or more sialic acids. The covalent addition of one or more sialic acids to peptides or glycopeptides can render the peptide or glycopeptides acidic.

Reverse phase, liquid Chromatography (RPLC) has been found to be an effective technique for analyzing peptides. It has been found, however, that many peptides, particularly acidic peptides can interact with metal oxides in the flow path of the chromatography system to create poor peak intensity, strong tailing, and a large amount of carryover. These side effects of the interaction of acidic peptides with metal oxides can lead to inaccurate analysis of the acidic peptides in a sample.

In one aspect, the flow path of a chromatographic system includes the interior surface of all tubing, adapters and columns from the sample injection needle to the detector. The flow path of the chromatographic system is defined, at least in part by, an interior surface of a sample injection needle, passageways through frits, interior surfaces of a chromatographic column, and interior surfaces of any tubing used to connect the components of the chromatographic system. A "metallic flow path" is a flow path that is composed wholly or partially of a metal, metal alloy, metal oxide, or combinations thereof.

FIG. 1 is a representative schematic of a chromatography system 100 that can be used to separate analytes, such as acidic peptides, in a sample. Chromatographic flow system 100 includes several components including a fluid manager system 105 (e.g., controls mobile phase flow through the system), tubing 110 (which could also be replaced or used together with micro fabricated fluid conduits), fluid connectors 115 (e.g., fluidic caps), frits 120, a chromatography column 125, a sample injector 135 including a needle (not shown) to insert or inject the sample into the mobile phase, a vial, sinker, or sample reservoir 130 for holding the sample prior to injection, an infusion system/detector 150, such as a mass spectrometer. Interior surfaces of the components of the chromatographic system/device form a fluidic flow path that has wetted surfaces. The fluidic flow path can have a length to diameter ratio of at least 20, at least 25, at least 30, at least 35 or at least 40.

In an embodiment, a method of separating and/or purifying acidic peptides includes injecting a sample having one or more polynucleotides into a chromatographic system. The chromatographic system includes components, as described above, which form a flow path for passage of the sample. In many chromatographic systems, particularly high pressure liquid chromatographic systems and ultra-high pressure liquid chromatographic systems, most, if not all, of the flow path is formed from a metal, creating a metallic flow path. Typical metals used include, but are not limited to, stainless steel and titanium. The metals used in chromatographic systems having metallic flow paths can be oxidized to metal oxides such as iron oxide, chromium oxide and titanium oxide. Thus, most chromatographic systems having a metallic flow path will have residual metal oxides covering at least a portion of the flow path.

Peptides in general, and specifically, acidic peptides are analyzed using reversed phase liquid chromatography. Reversed phase chromatography is a technique that uses a hydrophobic (non-polar) stationary phase and a polar (typically aqueous) mobile phase. The mobile phase, in some embodiments, is composed of an eluent in a solvent. The "eluent" is the carrier portion of the mobile phase. The eluent displaces the analyte from the sorbent allowing the analyte to travel through the stationary phase of the chromatography column. A "polar mobile phase" is, in some embodiments, composed of a polar solvent and a polar eluent. However, in other embodiments, a polar mobile phase may be composed of a polar eluent in a non-polar solvent, or a non-polar eluent in a polar solvent. A polar mobile phase has a dielectric constant of 15 or more. In reversed phase chromatography, hydrophilic molecules will generally move through the stationary phase faster than hydrophobic molecules, which is the reverse of normal-phase chromatography.

In one embodiment, a sample that includes acidic peptides is analyzed using reversed phase liquid chromatography and mass spectrometry (MS). Mass spectroscopic analysis of peptides generally works best if the peptides are positively charged. To ensure that a peptide is positively charged, traditional RPLC-MS peptide mapping chromatographic methods use C18 column chemistry with mobile phases composed of, for example, water, acetonitrile, and an acid (e.g., formic acid). The acid is added to ensure that the peptides in the sample are protonated, which will boost the electrospray ionization (ESI+) of the peptide analytes and thus increase the sensitivity of mass spectrometry detection. As noted above, however, under acidic pH mobile phase conditions, the acidic peptides interact with residual metal oxides via chelation reactions. This interaction leads to significant or complete loss of signal for the acidic peptides in a typical RPLC-MS analysis.

In an embodiment of the invention, the problems associated with an acidic mobile phase can be overcome by using a "neutral mobile phase." As used herein, a "neutral mobile phase" is a mobile phase having a pH greater than or equal to the isoelectric point of one or more of the metal oxides in the flow path. For typical chromatographic systems, a neutral mobile phase will have a pH greater than or equal to about 4, greater than or equal to about 5, greater than or equal to about 5.5, greater than or equal to about 6, greater than or equal to about 6.5, greater than or equal to about 7, greater than or equal to about 7.5, or greater than or equal to about 8. In some embodiments, the pH of a neutral mobile phase may be between about 4 and about 8, between about 5 and about 8, between about 6 and about 8, between about 6.5 and about 8, or between about 7 and about 8. A basic mobile phase (pH greater than 8) may also be used. However, an upper limit for the pH of the mobile phase may be required if the column sorbent decomposes under basic conditions. Use of a neutral mobile phase inhibits the formation of positively charged metal oxides. Reducing or eliminating the amount of positively charged metal ions will inhibit potential ion exchange reactions between the acid chains of the peptides and the metal oxides. This leads to minimized loss of acidic peptides in the chromatographic system.

The mobile phase, in an embodiment, may be a solution of a salt that can render the metal oxides neutral. For example, an aqueous ammonium acetate solution can be used to create a mobile phase that has a pH of about 7.0. An aqueous solution of ammonium acetate exerts a moderating buffering effect in the presence of metal oxides and acidic peptides. Other volatile salts that have moderating buffering effects include ammonium bicarbonate (pH 7.9) and ammonium carbonate (pH 8.5).

A buffered aqueous solution can be used to form a mobile phase. Preferably, a buffered aqueous solution includes volatile components suitable for MS analysis. Examples of buffered solutions include trimethylamine/HCl (pH range is 6.8 to 8.8); ammonia/formic acid (pH range is 7 to 8.5); trimethylamine/carbonate (pH range is 7 to 12).

Neutral phase mobile phases in reversed phase chromatography is particularly useful for the separation and/or analysis of acidic peptides. In some embodiments, neutral phase mobile phase reversed phase chromatography is used for the analysis of glycopeptides and sialylated glycopeptides. In some embodiments, neutral phase mobile phase reversed phase chromatography is used for the analysis of phosphopeptides. The use of neutral phase mobile phase reversed phase chromatography has been found to be successful for improving signal strength and recovery of acidic peptides.

After the sample passes through the chromatography column, the fluid stream from the chromatographic column passes to detector 150. Detector 150 can be, for example, a UV-Vis diode array detector, a mass spectrometer, or a combination of both. Any other type of detector can be used as well. For the analysis of acidic peptides, detector 150 is preferably a mass spectrometer.

Electrospray ionization (ESI) mass spectrometry is a common tool for the analysis of biological molecules, particularly peptides. Traditionally, acidic additives (e.g., formic acid) are added to the mobile phase of the RPLC to increase the sensitivity of mass spectrometry detection. As noted previously, however, under acidic mobile phase conditions, the acidic peptides interact with residual metal oxides. The use of a neutral mobile phase can overcome the interaction of acidic peptides with the metal oxides, but at the potential loss of sensitivity of the mass spectrometer. In one embodiment, this loss of sensitivity may be overcome by addition of an acid solution (e.g., aqueous formic acid) to the fluid stream that is exiting the chromatographic column of the chromatographic system. The addition of an acidic solution can be used to boost ESI signals for MS detection.

Figure 2:
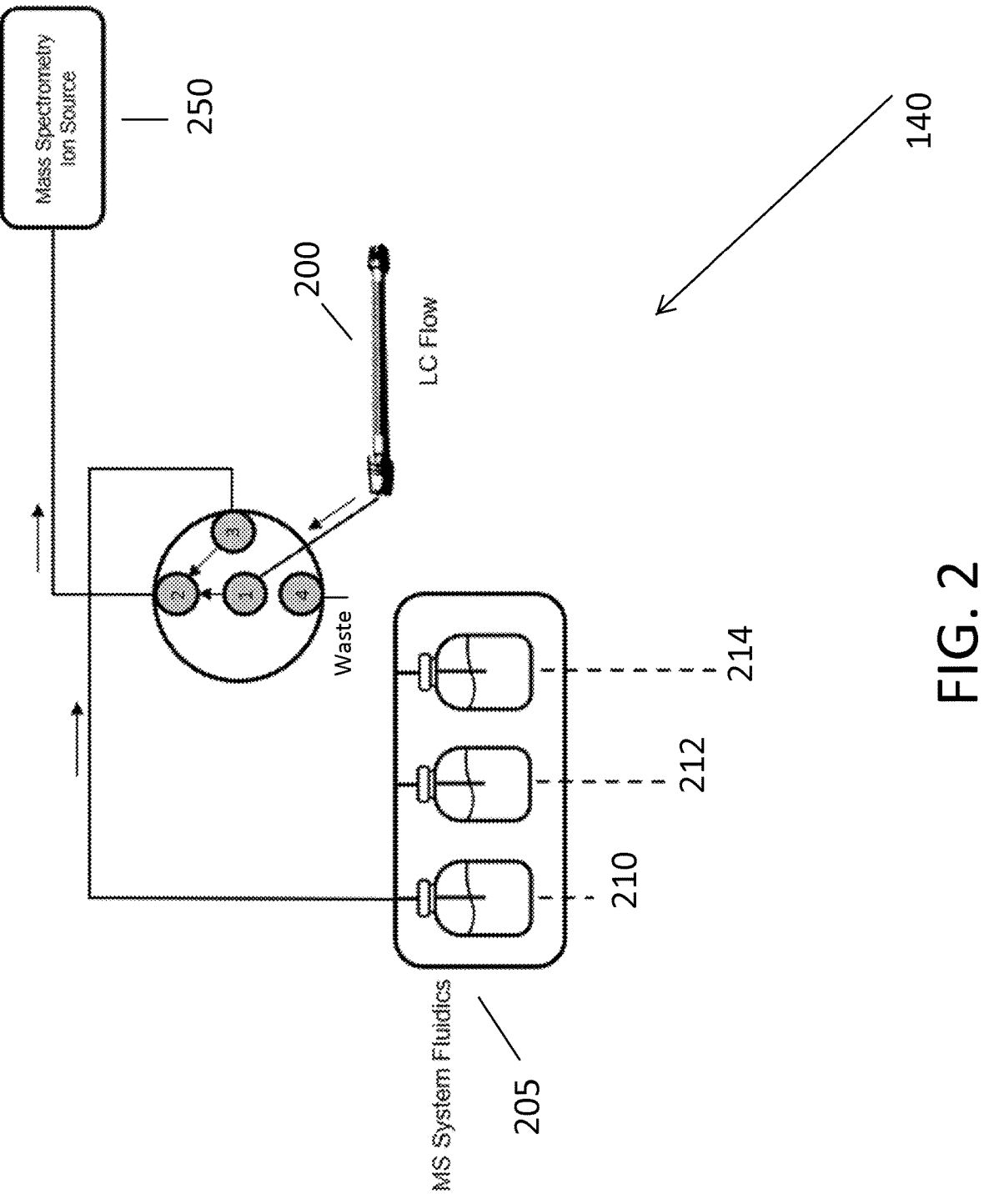
FIG. 2 depicts a schematic diagram of an infusion system useful for mass spectrometry analysis of the acidic peptides.

FIG. 2 depicts a schematic diagram of infusion system 140 useful for mass spectrometry analysis of the acidic peptides. An infusion system includes the mass spectrometer fluidics 205 (MS System Fluidics) which includes storage containers (210, 212, and 214) which store, in some embodiments, an acidic solution, a lock mass calibration solution, and a system calibration solution, respectively. During use diverter valve port 1 receives the fluid stream from the chromatographic system 200. Diverter valve port 3, substantially simultaneously receives an acidic solution stream from the MS System fluidics (Container 210). The neutral pH sample stream and the acidic solution stream are mixed with each other and exit the diverter valve through port 2. The resulting mixed stream is then sent to the mass spectrometry ion source 250 for ESI analysis. Port 4 is used as a waste port.

The acidic solution may include any acid, however, volatile acids are preferred. Examples of volatile acids include, but are not limited to formic acid and acetic acid. Formic acid, being one of the more volatile acids is generally preferred. In an embodiment, the concentration of the acid component of the acidic solution is between about 1% and 20% by volume in water. During mixing, the concentration of acid in the mixed stream may be adjusted by altering the concentration of the acid component of the acidic solution, altering the flow rate of the acidic solution, or a combination of both. The flow rate of the acidic solution may be varied between about 1 μL/min to about 50 μL/min, with the flow rate of the sample stream from the chromatographic system ranging from 50 μL/min to 200 μL min. In some embodiments, the ratio of the flow rate of the acidic solution to the flow rate of the fluid stream from the chromatographic system is between about 1:100 and about 1:5; between about 1:50 and about 1:5; between about 1:25 and about 1:5; or between about 1:10 and 1:5.

As a further, optional, improvement to the separation and/or purification of acidic peptides, various portions of the flow path of the chromatographic system can be coated with a low-bind surface coating. One method of coating metal flow path components with a low-bind surface coating is the use of alkylsilyl coatings. In some aspects, the alkylsilyl coating acts a bioinert, low-bind surface coating to modify a flow path to address flow path interactions with an analyte, such as an acidic protein. That is, the bioinert, low-bind surface coating minimizes surface reactions of the acidic peptide with the metal oxides and allows the sample to pass along a flow path without clogging, attaching to surfaces, or change in analyte properties. The reduction/elimination of these interactions is advantageous because it allows for accurate quantification and analysis of acidic peptides.

The alkylsilyl coating can be provided throughout the system from the tubing or fluid conduits 110 extending from the fluid manager system 105 all the way through to the detector 150. The coatings can also be applied to portions of the fluidic fluid path (e.g., at least a portion of the fluidic path). That is, one may choose to coat one or more components or portions of a component and not the entire fluidic path. For example, the internal portions of the chromatography column can be coated whereas the remainder of the flow path can be left unmodified.

Further information regarding the coating and the deposition of coatings in accordance with the present technology is available in U.S. Patent Application Publication No. 2019/0086371, which is hereby incorporated by reference.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Etanercept is a highly sialylated O-glycopeptide which has been previously observed in RPLC only after the sialic acid moieties have been enzymatically removed to avoid adsorption to metal oxides in the LC system. Samples of etanercept were reduced, alkylated, and digested with trypsin prior to analysis. Four tests were run to study the ability to analyze etanercept using RPLC. Test A uses an acidic mobile phase on a CSH C18 column having a low-bind surface coating (available from Waters Corporation, Milford, MA; Premier CSH, 130 Å, 1.7 μm, 2.1×100 mm) at 65° C. Test B uses a neutral mobile phase on a CSH C18 column having a low-bind surface coating (available from Waters Corporation, Milford, MA; Premier CSH, 1.7 μm, 2.1×100 mm) at 65° C. Test C uses an acidic mobile phase on a traditional CSH C18 column (no low-bind coating) at 65° C. Test D uses a neutral mobile phase on a on a traditional CSH C18 column (no low-bind coating) at 65° C. For the acidic mobile phase, mobile phase A (MPA) was 0.1% formic acid in water and mobile phase B (MPB)

was 0.1% formic acid in acetonitrile. For the neutral mobile phase, mobile phase A (MPA) was a neutral pH ammonium acetate buffer and mobile phase B (MPB) was 100% acetonitrile. For tests performed using a neutral mobile phase, post-column infusion of formic acid solution is employed to improve MS detection by DIA (MS$^E$) via QTOF MS and DIA with Ion Mobility (HDMS$^E$) via Cyclic Ion Mobility MS. ECD was applied for glycosylation site identification.

Figure 3A:
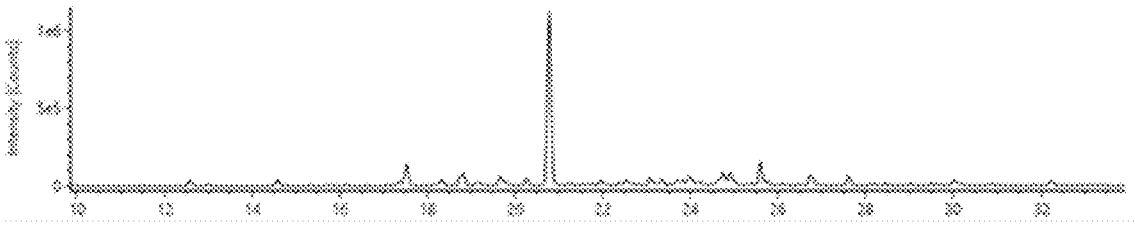
FIG. 3A depicts an extracted ion chromatogram obtained during the analysis of etanercept using a low-bind surface coated CSH column with acidic mobile phases (i.e., available from Waters Corporation, Premier CSH column).
Figure 3B:
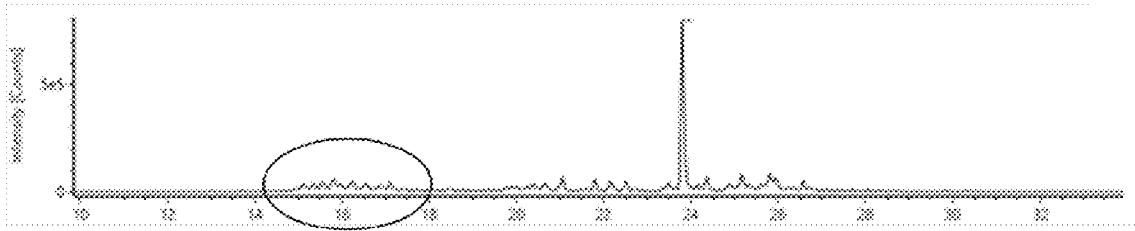
FIG. 3B depicts an extracted ion chromatogram obtained during the analysis of etanercept using a low-bind surface coated CSH column with neutral mobile phases.
Figure 3C:
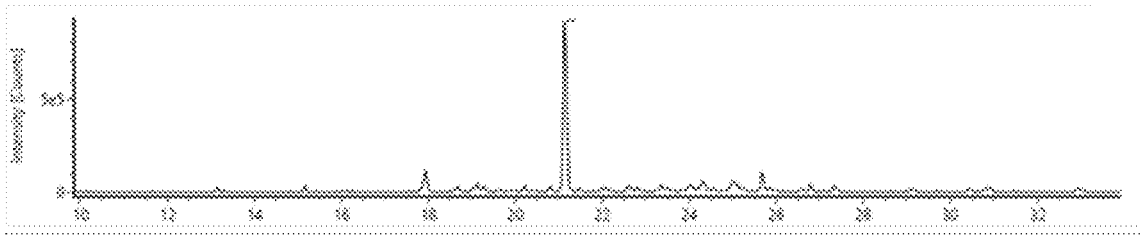
FIG. 3C depicts an extracted ion chromatogram obtained during the analysis of etanercept using a traditional CSH column with acidic mobile phases (i.e., column does not include low-bind surface coating).
Figure 3D:
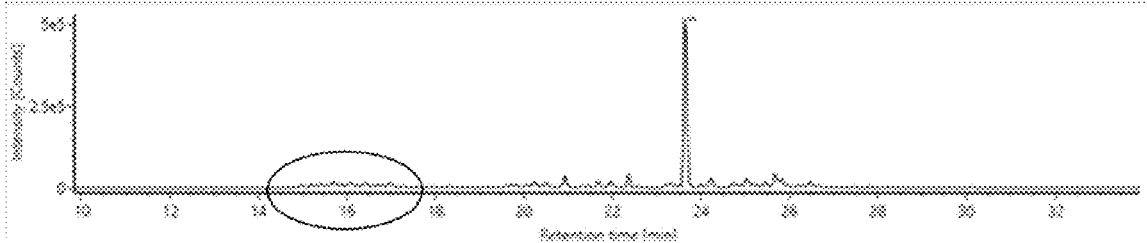
FIG. 3D depicts an extracted ion chromatogram obtained during the analysis of etanercept using a traditional CSH column with neutral mobile phases.

During CID fragmentation, sialylated peptides generate oxonium ions with m/z 292 & 274, and these can therefore be used as diagnostic ions for the presence of sialic acid. FIG. 3A, FIG. 3B, FIG. 3C and FIG. 3D show extracted ion chromatograms in the high energy channel for these oxonium ions for etanercept tryptic digest. FIG. 3A provides the results from a Premier CSH column (available from Waters Corporation, Milford, MA) with acidic mobile phases; FIG. 3B provides the results from a Premier CSH column (available from Waters Corporation, Milford, MA) with neutral mobile phases; FIG. 3C provides the results from a traditional CSH column with acidic mobile phases; and FIG. 3D provides the results from a traditional CSH column with neutral mobile phases. The highly sialylated peptide species are detected using neutral mobile phases for both Premier (available from Waters Corporation, Milford, MA) and non-Premier CSH columns (circled regions of FIG. 3B and FIG. 3D) and are not detected in acidic mobile phase conditions (FIG. 3A and FIG. 3C).

The neutral mobile phase RPLC-MS method is successful in recovering highly acidic peptides which are not detected by the conventional acidic mobile phase RPLC-MS. Most notably, this method has enabled the successful detection and characterization of the complex highly sialylated tryptic O-glycopeptides of etanercept T20 peptide. To our knowledge, this is the first report of successful LC-MS detection of O-glycosylated T20 peptides without any removal of the sialic acid moieties before analysis. Previous published work on the etanercept O-glycosylation (site identification), which used sialidase to remove the sialic acids from the O-glycans linked to the tryptic peptide, suggest that this peptide contains 5-7 occupied O-glycosylation sites (See Houel et al. "N- and O-Glycosylation Analysis of Etanercept Using Liquid Chromatography an Quadrupole Time-of-Flight Mass Spectrometry Equipped with Electron-Transfer Dissociation Functionality" *Anal Chem.* 2014, 86, 576-584). This is confirmed and expanded upon with neutral mobile phase RPLC-MS analysis, as this peptide was observed with primarily 6-7 O-glycosylation sites with up to 11 sialic acids present, for a total of 16 different O-glycopeptide species detected. The species with the highest relative abundance were T20+7 N-acetylhexosamine (HexNAc)+7 hexosamine (Hex)+8 N-acetyl-neuraminic acid (NeuAc) and T20+7 HexNAc+7 Hex+9 NeuAc, with greater than 15% for each component. Furthermore, the use of alternative fragmentation methods which keep the glycan intact, such as electron capture dissociation (ECD), can be used to explore the O-glycan site location and structure.

Figures 4A, 4B:
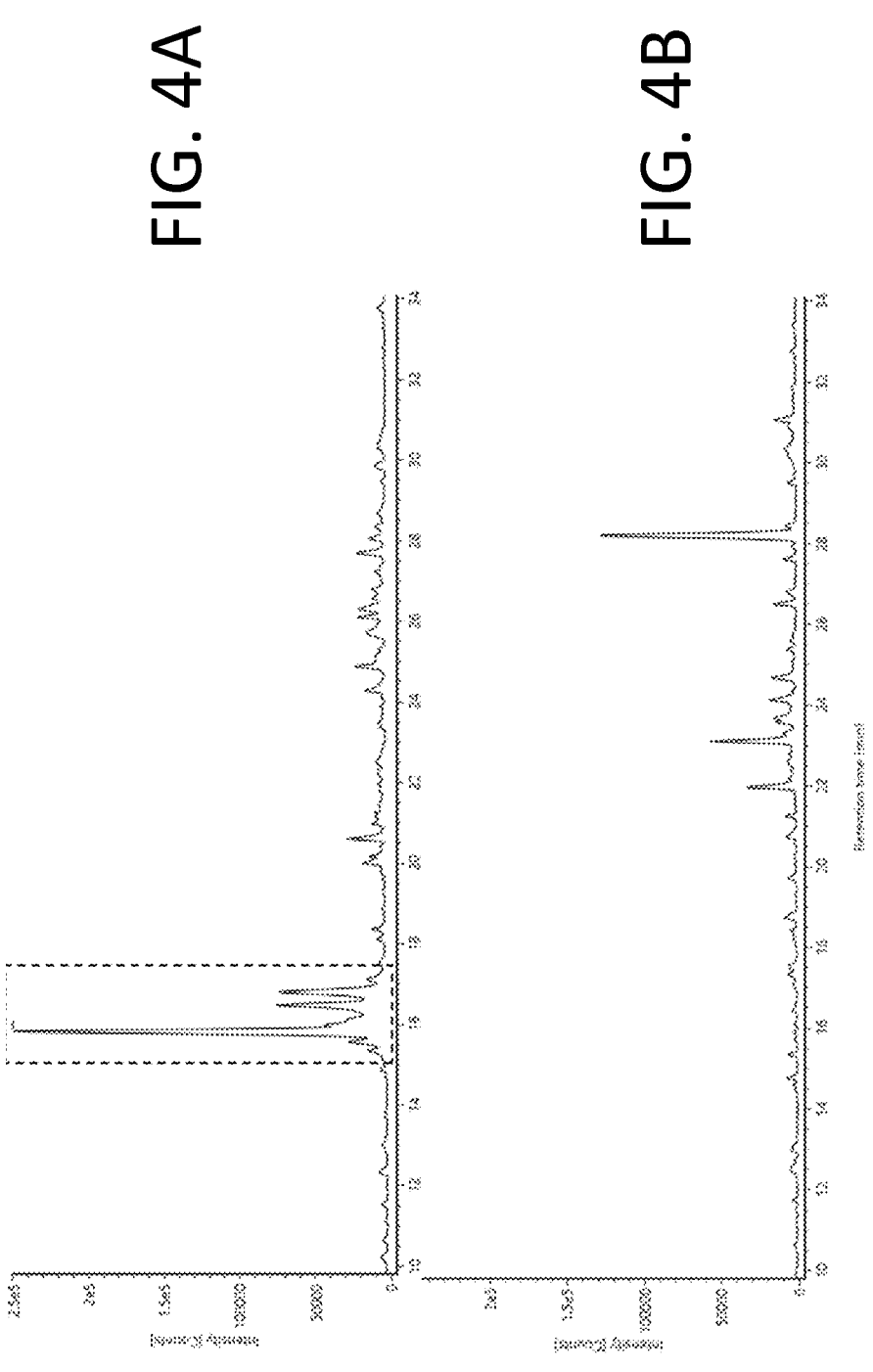
FIG. 4A depicts an extracted ion chromatogram obtained for one of the most prominent sialylated T20 O-glycopeptides+7HexNAc+7Hex+8NeuAc; m/z 1730.09, 5+& m/z 1441.9, 4+ detected via neutral mobile phase reverse phase chromatography.
FIG. 4B depicts an extracted ion chromatogram obtained for one of the most prominent sialylated T20 O-glycopeptides+7HexNAc+7Hex+8NeuAc; m/z 1730.09, 5+& m/z 1441.9, 4+ detected via with acidic mobile phase on a low-bind surface coated CSH column.

FIG. 4A and FIG. 4B depict extracted ion chromatograms for one of the most prominent sialylated T20 O-glycopeptides T20+7HexNAc+7Hex+8NeuAc; m/z 1730.09, 5+& m/z 1441.9, 4+) detected via neutral mobile phase reverse phase chromatography (FIG. 4A), compared with acidic mobile phase reverse phase chromatography (FIG. 4B) on the Premier CSH column (available from Waters Corporation, Milford, MA).

Example 2

Beta casein is a phosphorylated peptide. Samples of beta casein were reduced, alkylated, and digested with trypsin prior to analysis. Two tests were run to study the ability to analyze beta casein using RPLC. Test A uses an acidic mobile phase on a CSH C18 column having a low-bind surface coating (available from Waters Corporation, Milford, MA; Premier CSH, 130 Å, 1.7 μm, 2.1×100 mm) at 65° C. Test B uses a neutral mobile phase on a CSH C18 column having a low-bind surface coating (available from Waters Corporation, Milford, MA; Premier CSH, 1.7 μm, 2.1×100 mm) at 65° C. For the acidic mobile phase, mobile phase A (MPA) was 0.1% formic acid in water and mobile phase B (MPB) was 0.1% formic acid in acetonitrile. For the neutral mobile phase, mobile phase A (MPA) was a neutral pH ammonium acetate buffer and mobile phase B (MPB) was 100% acetonitrile. For tests performed using a neutral mobile phase, post-column infusion of formic acid solution is employed to improve MS detection.

Figures 5A, 5B:
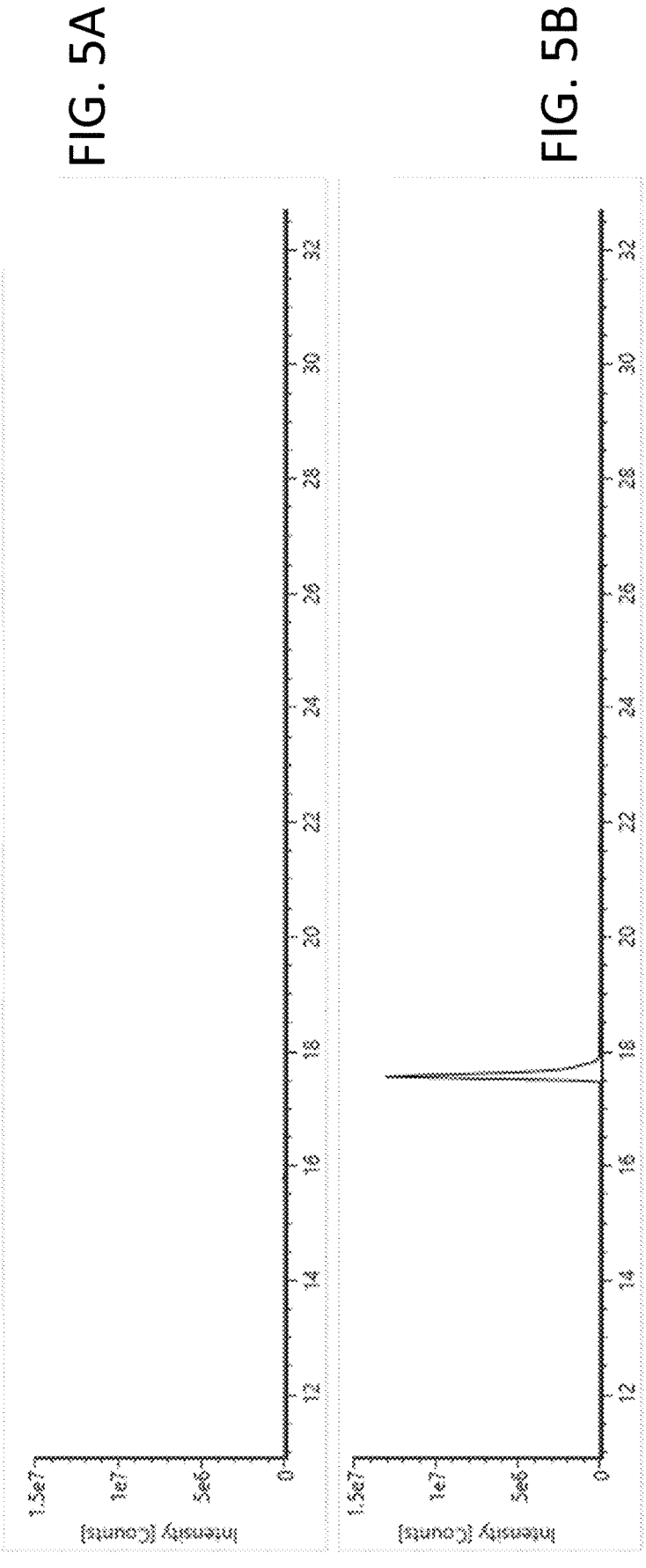
FIG. 5A depicts an extracted ion chromatogram (m/z 1041.4 & 1561.6) for 4× phosphorylated T1-2 peptide of beta casein tryptic digest on low-bind surface coated CSH column with acidic mobile phases.
FIG. 5B depicts an extracted ion chromatogram (m/z 1041.4 & 1561.6) for 4× phosphorylated T1-2 peptide of beta casein tryptic digest on low-bind surface coated CSH column with neutral mobile phases.

FIG. 5A and FIG. 5B depicts extracted ion chromatograms (m/z 1041.4 & 1561.6) for 4× phosphorylated T1-2 peptide of beta casein tryptic digest on the Premier CSH (available from Waters Corporation, Milford, MA). FIG. 5A shows extracted ion chromatogram for analysis of beta casein tryptic digest on a Premier CSH column with acidic mobile phases. FIG. 5B shows extracted ion chromatogram for analysis of beta casein tryptic digest on a Premier CSH column with neutral mobile phases. As can be seen in Panel A, beta casein tryptic digest is not detected using acidic mobile phase RPLC-MS method. However, beta casein tryptic digest was detected with high MS signals using neutral mobile phase RPLC-MS.

Example 3

NIST mAB N-glycopeptides were separated on a CSH C18 column having a low-bind surface coating (available from Waters Corporation, Milford, MA; Premier CSH, 130 Å, 1.7 μm, 2.1×100 mm). Three tests were run to study the ability to analyze beta casein using RPLC. Test A uses an acidic mobile phase on a CSH C18 Premier column. Test B uses a neutral mobile phase on a CSH C18 Premier column (available from Waters Corporation, Milford, MA). Test C uses a neutral mobile phase on a CSH C18 Premier column (available from Waters Corporation, Milford, MA) with post column infusion of formic acid (about 0.09% formic acid) prior to MS analysis. For the acidic mobile phase, mobile phase A (MPA) was 0.1% formic acid in water and mobile phase B (MPB) was 0.1% formic acid in acetonitrile. For the neutral mobile phase, mobile phase A (MPA) was a neutral pH ammonium acetate buffer and mobile phase B (MPB) was 100% acetonitrile.

Figures 6A, 6B, 6C:
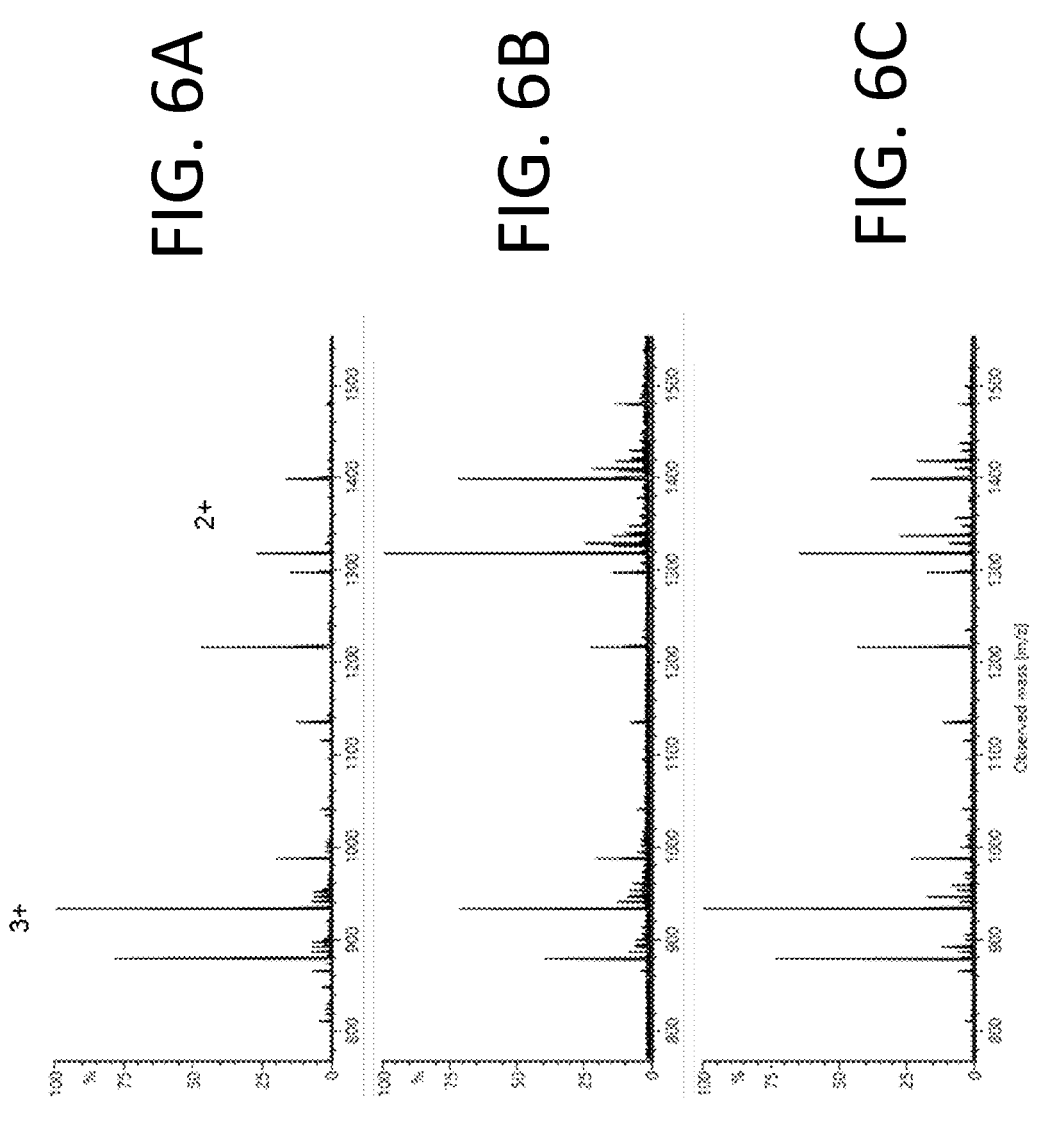
FIG. 6A depicts a MS spectrum for NIST mAb N-glycopeptides separated on a low-bind surface coated CSH column with acidic mobile phases (0.1% formic acid).
FIG. 6B depicts a MS spectrum for NIST mAb N-glycopeptides separated on a low-bind surface coated CSH column with neutral mobile phases.
FIG. 6C depicts a MS spectrum for NIST mAb N-glycopeptides separated on a low-bind surface coated CSH column with neutral mobile phases with post column infusion of formic acid (~0.09% formic acid at MS source).

FIG. 6A, FIG. 6B and FIG. 6C depicts combined MS spectra for NIST mAB N-glycopeptides. FIG. 6A shows combined MS spectra for NIST mAB N-glycopeptides for analysis on a Premier CSH column with acidic mobile phases. FIG. 6B shows combined MS spectra for NIST mAB N-glycopeptides for analysis on a Premier CSH column with neutral mobile phases. FIG. 6C shows combined MS spectra for NIST mAB N-glycopeptides for analysis on a Premier CSH column with neutral mobile phases with post column infusion of formic acid. These tests show a shift to lower charge state in the neutral mobile phase analysis (compare FIG. 6A to FIG. 6B), which is successfully shifted back towards 3+ when formic acid is infused post-column (as compared to FIG. 6C).

Conclusion

This data shows this new RPLC-MS approach, which employs a neutral pH mobile phase, not only recovers highly acidic peptides effectively, but also maintains good chromatographic performance for other types of peptides (e.g. neutral or basic).

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of separating sialylated O-glycopeptides, the method comprising:

injecting a sample comprising a plurality of O-sialylated glycopeptides into a chromatographic system, the chromatographic system comprising a flow path, wherein at least a portion of the flow path comprises one or more metal oxides, wherein the O-sialylated glycopeptides have three or more sialylation sites per peptide; and flowing the sample through the chromatographic system under reverse phase chromatography conditions to separate the plurality of O-sialylated glycopeptides using a mobile phase having a pH of about 6.5 to about 8.5.

2. The method of claim 1, wherein the mobile phase comprises an acetate salt dissolved in water.

3. The method of claim 1, wherein the mobile phase comprises a buffered aqueous solution.

4. The method of claim 1, wherein the mobile phase has a pH between about 7 and about 8.

5. The method of claim 1, further comprising passing a fluid stream exiting the chromatographic column to a detector, wherein the fluid stream comprises one or more of the acidic peptides.

6. The method of claim 5, further comprising adding an acidic solution to the fluid stream prior to passing the fluid stream to the detector.

7. The method of claim 6, wherein the acidic solution comprises formic acid.

8. The method of claim 6, wherein the acidic solution has an acid concentration of between about 1% and 20% by volume in water.

9. The method of claim 6, wherein the ratio of the flow rate of the acidic solution to the flow rate of the fluid stream is between about 1:100 and about 1:5.

10. The method of claim 5, wherein the detector is a mass spectrometer.

11. The method of claim 1, wherein at least a portion of the flow path is coated with a low-bind surface coating.

12. The method according to claim 11, wherein the low-bind surface coating comprises an alkylsilyl coating.

* * * * *